United States Patent [19]

Markert-Hahn et al.

[11] Patent Number: 5,514,559
[45] Date of Patent: May 7, 1996

[54] IMMUNOLOGICALLY ACTIVE CONJUGATES AND METHOD FOR THEIR PREPARATION

[75] Inventors: Christine Markert-Hahn, Seeshaupt; Beatus Ofenloch-Haehnle, Wielenbach; Eva Hoess, Starnberg; Erasmus Huber, Finning, all of Germany

[73] Assignee: Boehringer Mannheim GmbH, Mannheim, Germany

[21] Appl. No.: 219,468

[22] Filed: Mar. 29, 1994

[30] Foreign Application Priority Data

Mar. 29, 1993 [DE] Germany .................... 43 10 142.9

[51] Int. Cl.$^6$ .................... G01N 33/547; C12N 9/96; C07K 16/18
[52] U.S. Cl. .................... 435/7.92; 435/7.5; 435/188; 436/512; 436/532; 530/391.5; 530/391.9; 530/807; 530/811
[58] Field of Search .................... 435/7.5, 188, 7.92; 530/391.9, 807, 391.5, 811; 436/512, 532

[56] References Cited

U.S. PATENT DOCUMENTS

| | | | |
|---|---|---|---|
| 5,082,930 | 1/1992 | Nicolotti et al. | 530/402 |
| 5,091,542 | 2/1992 | Ahlem et al. | 548/521 |
| 5,168,057 | 12/1992 | Oh et al. | 435/174 |

FOREIGN PATENT DOCUMENTS

| | | |
|---|---|---|
| 0446017A2 | 3/1991 | European Pat. Off. . |
| 618192 | 10/1994 | European Pat. Off. . |
| 22583 | 12/1992 | WIPO . |

OTHER PUBLICATIONS

ImmunoTechnology Catalog & Handbook 1990, Pierce Chemical Company, pp. E-4 to E-10 and C-20 to C-27.

*Primary Examiner*—Mary E. Ceperley
*Attorney, Agent, or Firm*—Nikaido, Marmelstein, Murray & Oram

[57] ABSTRACT

Novel conjugate of the general formula $$A-L_1-L_2-B$$

wherein A and B are the substances to be coupled selected from the groups of haptens, proteins, polysaccharides, soluble polystyrenes, or peptides, $L_1$ and $L_2$ are trivalent linkers and $L_1$ and $L_2$ are bound via two thioether. They can be used in immunological assays and exhibit an improved storage stability.

13 Claims, No Drawings

IMMUNOLOGICALLY ACTIVE CONJUGATES AND METHOD FOR THEIR PREPARATION

Subject matter of the invention are immunologically active conjugates of haptens, proteins, and polymers which are bound in a stable form.

Numerous methods have been described for the binding of proteins, haptens, and polymers. Usually, two substances of this kind are covalently bound via bifunctional linkers. An overview of these methods is given by M. Brinkley in Bioconjugate Chem. 3 (1992) 2–13 and by Wong in Chemistry of protein conjugating and cross-linking, CRC press 1991. Particularly preferred is the coupling via formation of a thioether binding (MH-SH coupling) from a maleinimidyl group and a thiol group.

Often, however, the binding via such linkers is not stable and when these conjugates are stored in a liquid or a lyophilized form, they slowly degrade. This is particularly disadvantageous when the conjugates are used in immunoassays as this negatively affects sensitivity, accuracy, and precision of the measurement.

It is, hence, an object of the present invention to provide stable, immunologically active conjugates where substance to be conjugated exhibit a substantially more stable binding capacity than the linkers known from prior art.

This object is accomplished by conjugates having the general formula

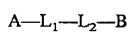

wherein A and B represent the substances to be coupled, selected from a group consisting of haptens, proteins (e.g. antibodies, enzymes, such as POD, β-galactosidase or alkaline phosphatase), polysaccharides (such as dextrane), soluble polystyrenes (e.g. lattices), or peptides (e.g. ED, β-galactosidase subunits), and $L_1$ and $L_2$ are trivalent linkers and wherein $L_1$ and $L_2$ are coupled via two thioether bindings.

Linkers $L_1$ and $L_2$ are chemical compounds consisting of three side arms (spacer) which are coupled via a C-atom. Each of these side arms of linker $L_1$ contains a maleinimido group and each of the two side arms of linker $L_2$ contain a thiol group. In order to couple substances A and B via linkers $L_1$ and $L_2$, the two maleinimido groups and the thiol group are linked by adding the SH group to the maleinimide to form two thioether bindings.

In addition to the two maleinimido groups and the thiol groups, the linkers used in accordance with the invention contain another functional group suitable to bind the linkers to the coupling substances A and B (for example haptens, proteins, polymers, or peptides). Such groups are, for example, ester-activated groups, such as N-hydroxy ester groups, imidazolides pyridazolides, amino alkyl carboxylic acids or activated aryl ester groups (e.g. p-nitrophenyl ester). The preferred coupling group is N-hydroxy succinimide.

Preferably, two homobidental trifunctional linkers are used to couple substances A and B, where the first linker carries two maleinimido groups and a hydroxy succinimide or carbodiimidazolyl group and a second linker carries two thiol groups or thiol groups protected via acyl groups as well as a hydroxysuccinimide or carbodiimidazolyl group.

In order to prepare the conjugates of the invention, the substances to be coupled are preferably linked to one of the two homobidental trifunctional linkers via hydroxy succinimide or carbodiimidazolyl groups. In a second step, the maleinimido groups are reacted with the thiol groups to form two thioether bindings.

The methods used in these procedures are well-known to the experts and described in S. Mitra, J. Am. Chem. Soc. 101 (1979) 3097–3110, for example.

The activation of proteins via the N-hydroxysuccinimide group can, for example, be realized by means of nucleophilic substitution at the ε-amino group of the lysine side chain of proteins in a slightly alkaline buffer. To achieve this, one uses a 1- to 15-fold excess of linker referred to the amino groups of the protein to be derivatized. The N-hydroxy succinimide formed during the reaction and the excess linker are separated by means of dialysis or gel chromatography.

Amino-group-containing haptens can be reacted either in organic media, such as dioxane or DMF with the addition of triethylamine, or in buffer mixtures, preferably potassium phosphate buffer, pH 7.5, with equimolar quantities of linkers in accordance with the invention.

The three side groups (spacers) which form the linkers are understood to be chemical groups intended to ensure a suitable spatial arrangement of A, B, and the thioether groups and to maintain the water solubility of the conjugates of the invention.

Other compositions and lengths of the functional groups of the homobidental trifunctional linkers are irrelevant. Examples that have the same composition as these linkers are described in US patent 5 091 542 wherein the homobidental trifunctional linkers according to the invention cannot carry maleinimido functions as do the linkers according to US patent 5 091 542. Instead, they carry only two maleinimido groups, and, for example, a hydroxysuccinimide group or two thiol groups and one hydroxysuccinimide group. Other suitable linkers are described in U.S. Pat. No. 5 168 057, for example, but also have homobidentally structured coupling groups.

The same applies to the linkers described in U.S. Pat. No. 5,082,930.

Other suitable linkers are described in German Patent Application P 43 10 141.0 by Boehringer Mannheim GmbH which has the same priority as the present patent application. The subject matter of this patent application is the subject matter of the disclosure of the present patent application.

In a preferred manner, the spacer groups used in the linker are saturated or unsaturated alkyl groups which are interrupted by imide, ether, carbonyl or carboxyl groups. The lengths of three spacer groups is also irrelevant and basically determined by the fact to avoid sterical hindrance between A and B and during the formation of the thioether bindings. It is expedient for the spacer groups to contain between 2 and 40 atoms.

Another subject matter of the invention is a method of preparing the conjugates in accordance with the invention. Said method comprises a first step in which a first substance A is coupled with the homobidental trifunctional linker $L_1$, containing two maleinimido groups, and a second step wherein a second substance B is coupled with a homobidental trifunctional linker $L_2$ containing two thiol functional groups. Subsequently, the so activated substance to be coupled are linked by adding SH groups to maleinimide via two thioether bindings.

Yet another subject matter of the invention is the use of the conjugates of the invention for the determination of immunologically active substances in immunological tests.

In tests of this kind, the conjugates of the invention can, for example, be used to implement the binding of the analyte to a solid phase or the binding of the analyte to a label (e.g. enzymes).

Particularly preferred conjugates include antibody/enzyme conjugates, antibody/biotin conjugates, hapten/biotin conjugates, antibody/antibody conjugates, avidin/streptavidin/antibody conjugates, avidin/streptavidin-haptenconjugates.

The following examples are given to explain the invention:

EXAMPLE 1

S, S-Diacetyl-6,8-dimercapto-octanoyl biphosphonate (biphosphonate-LIPOS)

102.1 mg (3 mmol) biphosphonate are dissolved in 7 mi of water and 155.8 mg (0.4 mmol) LIPOS (Example 2)in 4 ml of dioxane are added. The pH is adjusted to pH 6–7 using diluted ammonium and stirred for 24 hours at 20° C. Subsequently, another 78 mg (2 mmol) LIPOS are dissolved in 2 mi dioxane and added; 24 h later, another 39 mg (0.1 mmol) LIPOS are added. After a total of 4 days, the solvent is removed in a vacuum produced by a water pump, the residue is digested twice using 50 ml of THF each time and the supernatant is decanted. The raw product is dissolved in 0.5 ml of water, precipitated with methanol and dried in an exsiccator using $CaCl_2$.

Yield: 20 mg (12 % of theoretical) TLC: Cellulose, n-butanol/glacial acetic acid/water (v/v/v 3/1/1 ), detection using ninhydrin RF=0.58 $^1$H-NMR(D20/TMS-Na salt): d=1.30–2.00 (m, 10H, 5 $CH_2$); 2.23 (t, 2H, J=6.6 Hz, $CH_2CO$); 2.35 (s, 6H, $CH_3$-CO); 2.77 (s, 3H, N-$CH_3$); 2.77–3.70 ppm (m, 9H).

EXAMPLE 2

S, S-Diacetyl-6,8-dimercapto-octanoic acid-N-hydroxysuccinimide ester (LIPOS)

2.1 Dihydrolipoic acid 1.03 g (5 mmol) of lipoic acid are dissolved in 20 ml of water and 5 ml of ethanol, 380 mg (10 mmol) sodiumhydroboron are added and stirred at 200° C. After 60 min, another 380 mg (10 mmol) sodium hydroborum are added and stirred for another 5 hours at 20° C. The mixture is then diluted with 50 ml of water, adjusted to a pH of 1–2 using 1M hydrochloric acid and extracted twice with 50 ml of ethyl acetate. The combined organic phases are dried over sodium sulfate, the solvents are removed by distilling in a vacuum produced by a water pump and the oily residue is dried in a high vacuum.

Yield: 1.0 g (95 % of theoretical)

Analytic HPLC

Column: Vydac C18, 4.6×250 mm, 5 µm, 300 A

Alluting solvent:
  A: Millipore water, 0.01% TFA B: Acetonitrile, 0.01% TFA

Gradient: 0 -65 % B in 90 min

Flow: 1 ml/min

Detector: UV detection at 226 nm

Retention time: Dihydrolipoic acid 46.7 min

Lipoic acid 44.2 min

TLC: Silica gel (Merck 60), isopropyl ether/1% glacial acetic acid, detection with N-bromosuccinimide/fluorescein spray Rf=0.46 (educt Rf=0.43)

N-bromosuccinimideffluorescein spray:
  Spraying solution 1:0.2 % N-bromosuccinimide in methylene chloride
  Spraying solution 2:3 ml fluorescein solution (0.33 % fluorescein in 0.1N sodium hydroxide solution) dilute with 97 ml ethanol.

Detection:

Spray TLC with solution 1, allow to dry to 20° C., then spray with solution 2.

Coloration:

After extended standing times, pink dots on a yellow background indicate sulfur compounds.

2.2 S,S-Diacetyl-6,8-dimercapto-octanoic acids 1 g (4.75 mmol) dihydrolipoic acid (example 2.1) are dissolved in 50 ml of acetyl chloride and heated for 15 hours under reflux. Subsequently, the reaction solution is carefully poured on 500 ml ice water and extracted twice using 200 mi of ethyl acetate each time. The combined organic phases are dried over sodium sulfate, the solvent is removed by distilling in a vacuum produced by a water pump and the residue is purified by means of open column chromatography (silica gel Merck 60, 3×40 cm, eluent: ether/hexane (v/v 4/1 )/1% glacial acetic acid.

Yield: 860 mg (62 % of theoretical) TLC: Silica gel (Merck 60), isopropyl ether/1% glacial acetic acid, detection using N-bromosuccinimide/fluorescein spray Rf=0.45 (educt Rf=0.43) HPLC: Conditions see above Retention time: 52.0 min (di-acetate) 49.8 min (mono-acetate) $^1$H-NMR ($D_6$-DMSO/TMS): d=1.44 (m, 6H); 1.60 (m, 2H); 2.19 (t, 2H, J=6.8 Hz, $CH_2CO$); 2.31 (s, 6H, 2 $CH_3CO$); 2.85 (m, 2H, $CH_2$-S); 3.40 ppm (m, 1 H, CH-S).

2.3 S, S-Diacetyl-6,8-dimercapto-octanoic acid-N-hydroxy succinimide ester (LIPOS)

860 mg (2.94 mmol) of the compound according to example 2.2 are dissolved in 50 ml of absolute THF, then 372 mg (3.23 mmol) N-hydroxysuccinimide and 666 mg (3.23 mmol) dicyclohexycarbodiimide are added. After 3 hours of stirring at 20° C., another 115 mg (1 mmol) N-hydroxysuccinimide and 206 mg ( 1 mmol) DCC are added and stirring is continued for 24 hours at 20° C. Subsequently, the precipitated dicyclohexyl urea is removed by filtration, the filtrate is concentrated and added to 20 ml absolute THF. Insoluble components are removed by filtration and the solvent is removed by distilling. The residue is dissolved in 75 ml ethyl acetate and extracted twice using 40 ml of water each time. The ethyl acetate phase is dried over sodium sulfate, the solvent is removed in a vacuum produced by water, and the raw product purified by means of chromatography with silica gel (Merck 60, 4×30 cm, eluent: ethyl acetate/hexane (v/v 3/2). The pooled fractions are concentrated and the residue is dissolved in 20 ml dioxane and a lyophilisate is produced.

Yield: 820 mg (72 % of theoretical) TLC: Silica gel (Merck 60), ether/1% glacial acetic acid, detection with N-bromosuccinimide/fluorescein spray. Rf=0.36 $^1$H-NMR (D6-DMSO/TMS): d=1.30–1.89 (m, 8H); 2.31 (s, 6H, 2 $CH_3CO$); 2.59 (t, 2H, J=6.6 Hz, $CH_2CO$); 2.80 (s, 4H, 2 $CH_2CO$; 2.88 (m, 2H, $CH_2$-S); 3.40 ppm (m, 1H, CH-S).

EXAMPLE 3

3.1 N-α-Boc-ε-maleinimido-α-aminohexanoic acid (α-Boc-ε-Mal-Lys)

200 ml saturated sodium hydrogen carbonate solution are added to 3.70 g (15 mmol) of α-t-butyloxycarbonyl lysine, reacted with 2.54 g (15 mmol) N-ethoxycarbonyl-maleinimide and stirred for 30 min at 20° C. Subsequently, the reaction solution is diluted with 200 mi of water, adjusted to a pH of 1.8 using 2N hydrochloric acid, extracted twice with ethyl acetate using 200 ml each time, and dried over magnesium sulfate and the solvent is then removed by distilling in a vacuum produced by a water pump. The raw product is purified by means of open column chromatography (5×50 cm) over silica gel, eluent: ethyl acetate/methanol (v/v 4/1 )/1% acetic acid. The product containing fractions are purified, the solvent is removed in a vacuum produced by a water pump and the residue is dried in a high vacuum over $CaCl_2$.

Yield: 3.8 g (11.58 mmol) 78 % of theoreatical TLC: Silica gel (Merck 60), ethyl acetate/methanol (v/v 3/2)/1% acetic acid, detection with potassium permanganate Rf=0.83 $^1$H-NMR ($D_6$-DMSO/TMS): δ=1.35 (m, 15H, $^t$Bu u. 3 $CH_2$); 3.35 (m, 2H, $CH_2$-N); 3.66 (m, 1H, CH-N); 6.18 (d, br, 1H, NH, J=7.2 Hz); 6.98 ppm (s, 2H, CH=).

3.2 N-α-Boc-ε-maleinimido-α-aminohexanoyl-β-alanin (α-Boc-ε-Mal-Lys-β-Ala)

676 mg (5.92 mmol) N-hydroxysuccinimide and 1.21 g (5.92 mmol) dicyclohexylcarbodiimide are added to 1.60 g (4.9 mmol) of the compound of example 3.1 in 200 ml of THF and stirred for 20° C. at 1 hour. 480 mg (5.4 mmol) β-alanin are dissolved in 200 ml of 0.1M $KPO_4$ buffer, pH 8.5, and added dropwise to the reaction mixture. After 16 hours of stirring at 20° C., the organic solvent is removed by distilling in a vacuum produced by a water pump, the aqueous phase is diluted with 100 ml water, extracted twice with ethyl acetate using 250 ml each time, dried over magnesium sulfate and concentrated in a vacuum produced by a water pump. The residue is dried over a silica gel column (5×30 cm), the eluent is ethyl acetate/methanol (v/v 4/1 )/1% acetic acid.

Yield: 1.17 g (2.96 mmol) 61% of theoretical TLC: Silica gel (Merck 60), ethyl acetate/methanol (v/v 4/1 )/1% glacial acetic acid, detection with potassium permanganate $R_f$=0.7 $^1$H-NMR ($D_6$-DMSOITMS): δ=1.35 (m, 15 H, $^t$Bu u. 3 $CH_2$); 2.32 (t, 2H, $CH_2$CO, I=6.9 Hz); 3.16–3.41 (m, 4H, CH-N); 3.88 (m, 1H, CH-N); 6.73 (d, 1H, NH-COO, J=7.7 Hz); 6.98 (s, 2H, CH=); 7.78 ppm (t, 1H, NH-CO, I=5.4 Hz).

ε-Maleinimido-α-aminohexanoyl-p-alanin (ε-Mal-Lys-β-Ala)

15 ml trifluoro acetic acid are added to 710 mg (1.8 mmol) of the compound of the example 3.2 at 0° C. under stirring and then slowly heated up to 20° C. After 30 min, the solution is diluted with 15 ml of ethyl acetate and stirring is continued for another 15 min at 20° C. The solvent is then removed by distilling in a vacuum produced by a water pump and the residue is dissolved in ioxane/water (v/v 1/1) and a lyophilisate is produced.

Yield: 430 mg (1.5 mmol) 81% of theoretical TLC: Silica gel (Merck 60), ethyl acetate/methanol (v/v 1/4)/1% glacial acetic acid, detection with ninhydrin $R_f$=0.33 $^1$H-NMR ($D_6$-DMSO/TMS): δ=1.35–1.64 (m, 6H, 3 $CH_2$); 2.41 (t, 2H, CH2-CO, J=6.6 Hz); 3.37 (m, 4H, 2 $CH_2$-N); 3.68 (m, 1 H, CH-N); 7.00 (s, 2H, CH=); 8.53 ppm (t, 1H, NH-CO, I=6.0 Hz).

3.4 N-α-(6-maleinimidohexanoyl)-ε-maleinimido-α-aminohexanoyl-β-alanin (ε-MHS-ε-Mal-Lys-β-Ala)

A solution of 462 mg (1.5 mmol) maleinimidohexanoic acid-N-hydroxysuccinimide ester (MHS) in 10 ml THF is added in dropwise to a solution consisting of 400 mg (1.35 mmol) of the compound of the example 3.3 in 10 ml of 0.1M $KPO_4$ buffer pH 7.5 under stirring. The pH is adjusted to a value of 7.5 using 1 N sodium hydroxide solution. After 16 hours of stirring at 20° C., the organic solvent is removed by distilling in a vacuum produced by a water pump, the residue is diluted with 10 ml of water and adjusted to a pH of 3.0 using 1 N hydrochloric acid and extracted three times with ethyl acetate using 30 ml each time. The product is then converted into the organic phase. The phase is then dried with magnesium sulfate and concentrated in a vacuum produced by a water pump. The residue is purified by means of open column chromatography over silica gel, eluent ethyl acetate/methanol (v/v 2/1 )/1% acetic acid. The pooled fractions are concentrated and precipitated from 10 ml of ethyl acetate/THF (v/v 1/1 ) using diisopropylether. The precipitation is removed by filtration and concentrated in a high vacuum over $CaCl_2$.

Yield: 230 mg (0.47 mmol) 35% of theoretical TLC: Silica gel (Merck 60), ethyl acetate/methanol (v/v 2/1 )/1% glacial acetic acid, detection with potassium permanganate $R_f$=0.63 $^1$H-NMR ($D_6$-DMSO/TMS): δ=1.14–1.50 (m, 12H, 6 $CH_2$); 2.09 (t, 2H, $CH_2$-CO J=6.6 Hz); 2.22 (t, 2H, $CH_2$-CO, J=7.5 Hz); 3.37 (m, 6H, $CH_2$-N); 4.07 (m, 1H, CH-N); 7.00 (s, 2H, CH=); 7.85 ppm (m, 2H, NH-CO).

3.5 N-α-(6-maleinimidohexanoyl)-ε-maleinimido-α-aminohexanoyl-β-alanyl-(N-hydroxysuccinimide) (α-MHS-ε-Mal-Lys-β-Ala-OSu)

180 mg (0.36 mmol) of the compound of example 3.4 are dissolved in 10 ml of absolute DMF, 49 mg (0.43 mmol) N-hydroxysuccinimide and 60 μl (0.43 mmol) morpholino-ethyl isocyanate (MEI) added are and stirred for 16 hours at 20° C. Then 49 mg (0.43 mmol) N-hydroxysuccinimide and 60 μl (0.43 mmol) MEI were added twice, each time after 8 hours. To achieve a complete reaction, stirring was continued for another 6 hours. Subsequently, the solvent was removed in a high vacuum, the residue digested with 25 mi ethyl acetate, insoluble components removed by filtration and the filtrate concentrated to approximately 10 mi. The product dissolved in little ethyl acetate is added dropwise to 200 ml diisopropylether, the precipitated substance is removed (use the installed vacuum system only) washed with diisopropylether and drid in a drying chamber with $CaCl_2$.

Yield: 115 mg (0.20 mmol) 56 % of theoretical TLC: Silica gel (Merck 60), ethyl acetate/methanol (v/v 2/1 )/1% glacial acetic acid; detection with potassium permanganate $R_f$=0.83 $^1$H-NMR ($D_6$-DMSO/TMS): δ=1.06–1.50 (m, 12 H, 6 $CH_2$); 2.08 (t, 2H, $CH_2$CO, J=6.7 Hz); 2.50 (t, 2H, $CH_2$COOSu); 2.81 (s, 4H, 2 $CH_2$COO); 3.31 (m, 6H, 3 $CH_2$N); 4.12 (m, 1H, CH-NH); 6.98 (s, 4H, CH=); 7.81 (d, 1H, NHCH, J=7.0 Hz); 8.03 ppm (t, br, 1 H, $NHCH_2$)

EXAMPLE 4

Activation of PODp[1] using MALOS

Activation is carried out in a molar excess of MALOS (prepared according to example 3.5) to POD of 25:1. PODp at a concentration of 25 mg/ml is dissolved in 50 mM potassium phosphate buffer pH 7.5, 150 mM NaCl. The corresponding amount of MALOS was previously dissolved in DMSO using 100 mg/ml. 92 μl/ml of POD of this solution are added to the POD solution. The pH of this mixture is checked and adjusted to a value of 7.0, if necessary. Subsequently, the mixture is incubated for 1 h at 25° C. while stirring. The reaction is terminated by changing the pH to 6.1 and cooling the mixture in an ice-bath. Subsequently, non-coupled MALOS is removed in a flowing dialysis against 10 mM potassium phosphate buffer, pH 6.1, 50 mM NaCl, 1 mM EDTA. The incorporation of the MH groups is determined by reaction with a defined quantity of cystein and titration of the residual amount of cystein with dithiodipyridine.

[1] Prepolymerized POD (PODp) can be obtained by reacting monomer POD ($POD_{mono}$) with glutardialdehyde as described by Engvall and Perimann (Immunochemistry 8 (1971) 871–874)

EXAMPLE 5

Conjugation of PODp-MALOS with biphosphonate-LIPOS

1. Removing the acetyl-protective group in the bisphosphonate LIPOS by cleaving 1 mg biphosphonate LIPOS (manufactured according to example 1) is dissolved in 1 ml of 10 mM potassium phosphate buffer pH 7.5, 50 mM NaCl, 2 mM EDTA. 0.07 ml of a 1M hydroxylamine stock solution are added (final concentration 70 mM), and the mixture is then incubated for 1 hour at 25° C. under stirring.

2. Coupling with PODp-MALOS 3 mg PODp-MALOS are diluted in 3 ml of 10 mM potassium phosphate buffer pH 7.5, 50 mM NaCl, 2 mM EDTA. 0.044 ml of the above hydroxylaminolysis mixture are added (corresponds to a stoichiometry of biphosphonate to $POD_{mono}$ of 1:1); the mixture is incubated for 90 min at 25° C. while stirring. Subsequently, the reaction is terminated by successive incubation with cystein (2 mM) and N-ethyl-maleinimide (5 mM). The low-molecular components are separated in a flowing dialysis against 25 mM HEPES, pH 6.8, 150 mM NaCl.

EXAMPLE 6

Activation of biotin with MALOS 6.1 N-α-Boc-ε-maleinimido-α-aminohexanoyl-DADOO-biotin While stirring, 422 mg (3.67 mmol) N-hydroxysuccinimide and 757 mg (3.67 mmol) dicyclohexylcarbodiimide are added to a solution of 1.00 g (3.06 mmol) of the compound prepared according to example 3.1 in 50 ml THF. After stirring for 1 hour, a solution of 1.37 g (3.67 mmol) biotin-DADOO in 50 ml of 0.1M $KPO_4$ buffer pH 8.5 is added dropwise a temperature of 20° C. The mixture is stirred for another 2 hours at 20° C., subsequently, the organic solvent is removed in a vacuum produced by a water pump and the aqueous phase is lyophilized. The raw product is purified by means of silica gel chromatography, eluent ethyl acetate/methanol (v/v 2/1 )/1% acetic acid.

Yield: 930 mg (1.36 mmol) 44 % of theoretical TLC: Silica gel (Merck 60), ethyl acetate/methanol (v/v 2/1 )/1% glacial acetic acid Detection with biotin spray and potassium permanganate $R_f$=0.44 $^1$H-NMR ($D_6$-DMSO/TMS): d=1.10–1.90 (m, 15H, tBu and 6 $CH_2$); 2.06 (t, 2H, $CH_2CO$, J=6.7 Hz); 2.60–2.90 (m, 3H, CHS and $CH_2S$); 3.00–3.60 (m, 14H, 3 $CH_2N$ and 4 $CH_2O$); 3.77 (m, 1H, CHNH-Lys); 4.14 (dd, 1H, CH-NH-biotin); 4.14 (dd, 1H, CH-NH-biotin); 4.30(dd, 1H, CHNH-biotin); 4.30 (dd, 1 H, CHNH-biotin); 6.39 (m, 2H, NH-biotin); 6.76 (d, 1 H, NHCOO, I=7.1 ); 6.99 (s, 2H, CH=); 7.84 ppm (t, br, 2H, 2 NHCO).

6.2 ε-Maleinimido-α-aminohexanoyl-DADOO-biotin (ε-Mal-Lys-DADOO-biotin)

10 ml trifluoroacetic acid are added to 500 mg (0.7 mmol) of the compound prepared according to example 6.1 at 0° C. which is then slowly heated up to 20° C. After 30 min, the solution is diluted with 10 ml ethyl acetate and stirred for another 15 min. The solvent is removed in a vacuum produced by a water pump and the residue is dissolved in dioxane/water (v/v 1/1) and a lyophilisate is produced.

Yield: approx. 0.7 mmol TLC: Silica gel (Merck 60), ethyl acetate/methanol (v/v 1/1 )/1% glacial acetic acid Detection with biotin spray, potassium permanganate and ninhydrin $R_f$=0.08

6.3 N-α-maleinimidohexanoyl-ε-maleinimido-α-aminohexanoyl-DADOO-biotin (α-MHS-ε-MAL-Lys-DADOO-biotin)

0.7 mmol of the compound prepared according to example 6.2 (still contains TFA) are dissolved in 10 ml of 0.1M $KPO_4$ buffer pH 7.5 to which then 260 mg maleinimidohexanoic acid-N-hydroxysuccinimide (MHS) in 10 ml THF are added. The pH value is then adjusted to pH 7.5 using 1N sodium hydroxide solution until the pH value no longer changes. After stirring for 16 hours at 20° C., the organic solvent is removed in a vacuum produced by a water pump and the residue is lyophilized. The raw product is purified with silica gel, eluent ethyl acetate/methanol (v/v 1/1 )/1% acetic acid. The pooled fractions are concentrated in a vacuum produced by a water pump, the residue is dissolved in dioxane, insoluble components are removed by filtration and the mixture is then lyophilized.

Yield: 500 mg (still contains dioxane and acetic acid) TLC: Silica gel (Merck 60), ethyl acetate/methanol (v/v 1/1 )/1% glacial acetic acid Detection with biotin spray and potassium permanganate $R_f$=0.55 $^1$H-NMR (D20/TMS-Na-salt): d=1.20–1.80 (m, 18 H, 9 $CH_2$); 2.22 (m, 4H, 2 $CH_2CO$); 2.71–2.90 (m, 3H, CHS and $CH_2S$); 3.38–3.75 (m, 16H, 4 $CH_2N$ and 4 $CH_2O$); 4.20 (m, 1H, CHNH-Lys); 4.44 (dd, 1H, CHNH-biotin); 4.60 (dd, 1 H, CHNH-biotin); 6.88 ppm (s, 4H, CH=).

EXAMPLE 7

Storage stability of IgG-(MH)-biotin-(SH) conjugates and of IgG (MALOS)-biotin-LIPOS) conjugates 7.1 Activation of IgG with MALOS (see example 3.5) and MHS (maleinimidohexanoyl-N-hydroxysuccinimide ester)

Portions of 50 mg of the IgG were simultaneously reacted with MALOS and MHS (the IgG used is mouse-IgG from ascites, purified over ammonium sulfate precipitation and anionic exchange chromatography). The molar stoichiometry of IgG:MALOS and MHS was 1:25. MALOS and MHS had previously been dissolved in DMSO. The reaction was carried out in 50 mM potassium phosphate buffer/150 mM NaCl, pH 7.5. The concentration of the IgG was 25 mg/ml, the reaction temperature 25° C., reaction time 1 hour. In order to terminate the reaction, the pH of the reaction mixture was lowered to 6.1 and the mixture was dialyzed over night at 4° C. against 10 mM potassium phosphate buffer, 50 mM NaCl, 1 mM EDTA, pH 6.5. Subsequently, the incorporation of the MH groups was determined according to a known method (reaction of the MH groups with dithiodipyridine).

Result: IgG-MALOS: 5.5 mol MH/Mol IgG IgG-MH: 5.5 mol MH/Mol IgG 7.2 Biotinylation of the activated IgG with biotin-LIPOS or biotin-C11-SH In order to biotinylate the IgG-MALOS, the protected SH groups of the biotin-LIPOS were first released by hydroxylaminolysis:

5 mg/ml biotin-LIPOS were incubated in 25 mM hydroxylamine-containing buffer (10 mM potassium phosphate buffer, 50 mM NaCl, 2 mM EDTA, pH 7.5 for 1 h at 25° C.). Subsequently, the required amount of-biotin-LIPOS for the biotinylation were directly taken from this mixture.

To biotinylate the IgG-MH, the biotin-SH derivative was used directly. All the buffers used in the procedure were previously exposed to nitrogen to avoid oxidation of the free SH groups of the derivative as far as possible. Both biotinylation mixtures were prepared in different stoichiometries, each with 0.25:1, 0.5:1, and 1:1 (SH groups of the biotin derivative used to MH groups of IgG present).

The reaction was carried out at an IgG concentration of 1 mg/ml over 2 hours at 25° C. in 10 mM potassium phosphate buffer, 50 mM NaCl, 1 mM EDTA, pH 6.5. The reaction was stopped by adding N-methyl-maleinimide (final concentration 5 mM). Subsequently, all mixtures were dialyzed against 10 mM potassium phosphate buffer, 50 mM NaCl, pH 7.5 while flowing.

After this dialysis, the protein concentration of the mixtures was determined. Each mixture was treated as follows:

Adjusting to 0.8 mg/ml protein in 50 mM potassium phosphate buffer, 150 mM NaCl, pH 7.5. The solution was filtered until sterile and stored for stress at 35° C. and for checking at −80° C.

7.3 Checking the stability of the conjugates after exposure to stress

After 2 weeks, the biotin incorporation and the free biotin were determined in all mixtures.

The biotin incorporation was determined in an immunological test as follows: Each well (200 ng/ml) of a microtitre plate coated with streptavidin was incubated for 1 hour with 100 μl of IgG-Bi solution. Subsequently, unbound IgG-Bi was removed by washing. The bound IgG-Bi was detected by incubation with peroxidase-coupled streptavidin and ABTS®substrate for 1 hour. The biotin incorporation of the samples could be determined with the aid of a standard series of IgG with known degrees of biotinylation.

The free biotin was determined in an immunological test according to the following principle:

Biotin-coated tubes were incubated with peroxidase-coupled streptavidin. Bound streptavidin was detected by adding the POD substrate ABTS®. If the sample with a free biotin was added together with the SA-POD, the wall-bound streptavidin was replaced in dependency upon the contents of free biotin (first, the biotinylated IgG was precipitated from all samples with trichloroacetic acid; the supernatant was then used in the test). The biotin contents of the sample could then be read off a standard curve with free biotin.

To assess the storage stability of the various conjugates, the biotin incorporation was first calculated in mol of biotin per mol of IgG. Subsequently, the free biotin was determined in mol of biotin per mol of IgG. Then the percentage of released biotin was calculated after 2 weeks of storing at 34° C. based on the biotin incorporation when stored at −80° C.

The results are shown in the following table: In all SH:MH stoichiometries, the conjugates prepared in accordance with the claimed method were significantly more stable, usually by an average of the factor 10.

TABLE 1

Storage stability of the IgG—Bi conjugates

| Sample | Stoichiometry SH:MH | Storage temperature | Percent of biotin released |
|---|---|---|---|
| IgG(MH)—Bi(SH) | 0.25:1 | −80° C. | 4.1% |
| IgG(MH)—Bi(SH) | 0.25:1 | +35° C. | |
| IgG(MH)—Bi(SH) | 0.5:1 | −80° C. | 6.9% |
| IgG(MH)—Bi(SH) | 0.5:1 | +35° C. | |
| IgG(MH)—Bi(SH) | 1:1 | −80° C. | 5.6% |
| IgG(MH)—Bi(SH) | 1:1 | +35° C. | |
| IgG(MAL)—Bi(LIP) | 0.25:1 | −80° C. | 0.3% |

TABLE 1-continued

Storage stability of the IgG—Bi conjugates

| Sample | Stoichiometry SH:MH | Storage temperature | Percent of biotin released |
|---|---|---|---|
| IgG(MAL)—Bi(LIP) | 0.25:1 | +35° C. | |
| IgG(MAL)—Bi(LIP) | 0.5:1 | −80° C. | 0.5% |
| IgG(MAL)—Bi(LIP) | 0.5:1 | +35° C. | |
| IgG(MAL)—Bi(LIP) | 1:1 | −80° C. | 0.7% |
| IgG(MAL)—Bi(LIP) | 1:1 | +35° C. | |

Linkers which may be used as one of $L_1$ or $L_2$ are described in copending US. application filed of even date herewith entitled "Homobidental, Trifunctional Linkers, Method for their Preparation and Use in Immunologically Active Conjugates", U.S. Pat. No. 5,382,523, issued Jan. 17, 1995, the entire disclosure of which is hereby incorporated by reference.

We claim:

1. A conjugate of the formula $$A—L_1—L_2—B$$

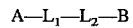

wherein A and B are substances to be coupled and are selected from the group consisting of haptens, proteins, peptides, polysaccharides and polystyrenes, and $L_1$ and $L_2$ are trivalent linkers, wherein $L_1$ and $L_2$ are linked to each other by two thioether bonds.

2. The conjugate according to claim 1, wherein A and B are linked to $L_1$ and $L_2$, respectively, by hydroxysuccinimide or carbodiimidazolyl residues.

3. The conjugate according to claim 1, wherein at least one of A and B are selected from the group consisting of antibodies, antibody fragments, enzymes, haptens, biotin, streptavidin and peroxidase.

4. An immunological assay using a bound analyte to bind to a specific binding partner thereof, the improvement comprising the use of a conjugate according to claim 1 as the bound analyte, wherein said analyte is A or B.

5. A method for producing a conjugate of the formula $$A—L_1—L_2—B$$

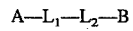

wherein A and B are substances to be coupled and are selected from the group consisting of haptens, proteins, peptides, polysaccharides and polystyrene, and $L_1$ and $L_2$ are trivalent linkers, wherein $L_1$ and $L_2$ are linked to each other by two thioether bonds, comprising the steps of linking a first substance A to be coupled to a homobidental, trifunctional linker $L_1$ containing two maleinimido groups to form $AL_1$, linking a second substance B to be coupled to a homobidental, trifunctional linker $L_2$ containing two thiol groups to form $BL_2$, and reacting the thiol groups of $BL_2$ with the maleinimido groups of $AL_2$ to form two thioether bonds linking $AL_1$ to $BL_2$.

6. The method according to claim 5, wherein A and B are linked to $L_1$ and $L_2$, respectively, via hydroxysuccinimide or carbodiimidazolyl groups.

7. The method according to claim 5, wherein at least one of A and B is selected from the group consisting of an antibody, an antibody fragment, an enzyme and a hapten.

8. The method according to claim 5, wherein one of A and B is selected from the group consisting of biotin, streptavidin and peroxidase.

9. The method according to claim 8, wherein the other of A and B is selected from the group consisting of antibodies, antibody fragments, enzymes and haptens.

10. The assay according to claim 4, wherein A is the analyte and B is a label or a support for A.

11. The conjugate according to claim 1, wherein at least one of A and B is selected from the group consisting of an antibody, an antibody fragment, an enzyme or a hapten.

12. The conjugate according to claim 1, wherein one of A and B is selected from the group consisting of biotin, streptavidin and peroxidase.

13. The conjugate according to claim 12, wherein the other of A and B is selected from the group consisting of antibodies, antibody fragments, enzymes and haptens.

* * * * *